US00PP29922P2

(12) United States Plant Patent
Korlipara

(10) Patent No.: US PP29,922 P2
(45) Date of Patent: Nov. 27, 2018

(54) ***ECHINACEA* PLANT NAMED 'TNECHKY'**

(50) Latin Name: ***Echinacea* spp.**
Varietal Denomination: TNECHKY

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/731,243

(22) Filed: May 9, 2017

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
See application file for complete search history.

*Primary Examiner* — Keith O. Robinson
(74) *Attorney, Agent, or Firm* — Klarquist Sparkman, LLP

(57) ABSTRACT

A new and distinct *Echinacea* plant named 'TNECHKY' characterized by an amazing number of large inflorescences starting in the first season, very long bloom time with excellent rebloom, a very upright, very compact habit, bright yellow ray florets surrounding green cones, ray florets held horizontally when young then dropping slightly, strong upright stems, and excellent vigor.

1 Drawing Sheet

Botanical denomination: *Echinacea* spp.
Variety designation: 'TNECHKY'.

BACKGROUND OF THE INVENTION

The present invention relates to a new and distinct cultivar of *Echinacea* and given the cultivar name 'TNECHKY'. *Echinacea* is in the family Asteraceae. The new cultivar is part of a planned breeding program for a container and edging series with compact habits and profuse inflorescences. The exact parents of this selection are unknown, unnamed, proprietary interspecific hybrids bred from *Echinacea paradoxa, Echinacea purpurea*, and *Echinacea tennesseensis*.

Compared to *Echinacea* 'Dixie Sun' (U.S. Plant Pat. No. 26,160), the new cultivar is shorter, with narrower leaves, produced more crowns from the base more quickly, and has ray florets that flare out straighter rather than cupping at the ends.

This new *Echinacea* cultivar is uniquely distinguished by:

1. an amazing number of large inflorescences starting in the first season,
2. very long bloom time with excellent rebloom,
3. very upright, very compact habit,
4. bright yellow ray florets surrounding green cones,
5. ray florets held horizontally when young then dropping slightly,
6. strong upright stems, and
7. excellent vigor.

This new cultivar has been reproduced only by asexual propagation (cuttings and tissue culture using shoot tips). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows an eight-month-old *Echinacea* 'TNECHKY' in flower growing in the trial field in full sun in early July in Canby, Oreg.

FIG. 2 shows a two-year-old *Echinacea* 'TNECHKY' in full bloom in mid-July in the trial field in full sun in Canby, Oreg.

DETAILED PLANT DESCRIPTION

The following is a detailed description of the new *Echinacea* cultivar based on observations of eight-month-old specimens growing in the trial bed in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* 5$^{th}$ edition, 2007.

Plant:

*Type*.—Herbaceous perennial.
*Hardiness*.—USDA Zones 4 to 9.
*Size*.—Grows to 33 cm wide and 31 cm tall to top of inflorescences.
*Form*.—Basal clump, with 8 to 9 stems from the base.
*Vigor*.—Excellent.
*Roots*.—Fibrous, with many downward growing and few laterals, ivory in color, Yellow White 158D, roots develop easily from cuttings from the crown.

Leaf (basal): Simple, lanceolate, blade grows to 17 cm long and 4.3 cm wide, margins sparsely serrate, apex acuminate, base attenuate , venation pinnate, both sides strigose, 137A with veins 145C on topside, 147B with veins 147C on bottom side; petiole clasping, to 8 cm long and 3 mm wide, strigose, 147C.

Leaf (stem):

*Type*.—Simple.

*Shape*.—Lanceolate.

*Arrangement*.—Alternate.

*Blade size*.—Grows to 13 cm long and 4.5 cm wide.

*Margins*.—Usually entire to sparsely serrate.

*Apex*.—Acuminate.

*Base*.—Attenuate.

*Surface texture*.—Strigose on both sides.

*Rugosity*.—Absent.

*Venation*.—Pinnate, Yellow Green 145C on both sides.

*Variegation*.—Absent.

*Color*.—Topside Green N137A, bottom side closest to Green 137B.

*Petiole description*.—Clasping, grows to 2 cm long and 7 mm wide, scabrous, narrow leafy edges, topside and bottom side Yellow Green 147C.

Inflorescence:

*Type*.—Daisy, composite on terminal stalked heads.

*Flowering stem*.—Grows to 29 cm tall from the base of the plant to the terminal leaves below peduncle; branched with flowering stems from base, branched with 3 to 7 inflorescences per stem; diameter growing to 10 mm wide near the inflorescence; strigose; Yellow Green 147B.

*Peduncle*.—Grows to 15 cm long from above terminal leaves to flower, 4 cm wide, strigose; Yellow Green 147B.

*Flowering stem strength*.—Strong.

*Size*.—Grows to 9 cm wide and 6.5 cm deep as disc enlarges.

*Form*.—Ray florets held horizontally when young, reflexing slightly when they mature, mature disc is conic.

*Immature inflorescence* (*bud*).—4 cm wide and 3 cm deep, ray florets held upright at a 40 degrees angle from vertical and rolled up so only the back color shows, Yellow Orange 16A, disc color Yellow Green 144A.

*Ray florets*.—Without pistil or stamen, 24 to 31 in number, grow to 40 mm long and 10 mm wide, oblanceolate to lanceolate with the tip two-to-three-toothed (each acute), entire margins, base attenuate, glabrous on both sides, semi-drooping attitude at origin; fully open florets topside closest to Yellow Orange 16A, bottom side 16B; florets lighten to topside 15B, bottom side 14C.

*Disc*.—Flat becoming conic, becoming 45 mm deep and 45 mm wide with maturity, Yellow Green 144A in background with bracts Yellow Orange 15A.

*Disc florets*.—To about 800 in number, each with 1 pistil and 4 stamen, grow to 8 mm long and 2 mm wide, each with one persistent, very stiff linear bract (13 mm long with the top 3 mm Yellow Orange 15A to 4 mm Yellow Green 144A to 6 mm of White NN155A on bottom); corolla 6 mm long and 2 mm wide, tubular, 5 lobed, glabrous and glossy, Yellow Green 144A at the base to Yellow Green 149D; pistil 9.5 mm long, ovary 4 mm long, White NN155D with top Yellow Green 144A, style 5.5 mm long and Yellow Green 149D, 2-branched stigma spreading 3 mm wide, Yellow Green 149D on bottom half and tinted Greyed Purple N186A on top half; stamen 4.5 mm long, filaments 2 mm long and White NN155B, anthers 3 mm long and Greyed Purple N186B, pollen none.

*Involucral bracts*.—In 4 leafy series, area grows to 35 mm wide and 7 mm deep, lobes lanceolate in shape, reflexed, grow to 8 mm long and 3 mm wide, both sides Green 137A, margins strigose, tip acute, strigose on both sides.

*Receptacle*.—Grows to 15 mm wide and 23 mm deep, White NN155B.

*Bloom period*.—June through October in Canby, Oreg.

*Fragrance*.—Slight, floral perfume.

*Lastingness*.—Each inflorescence lasts about two weeks in Canby, Oreg.

Seeds: 3 mm long and 2.5 mm wide, oval, Brown 200C.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *

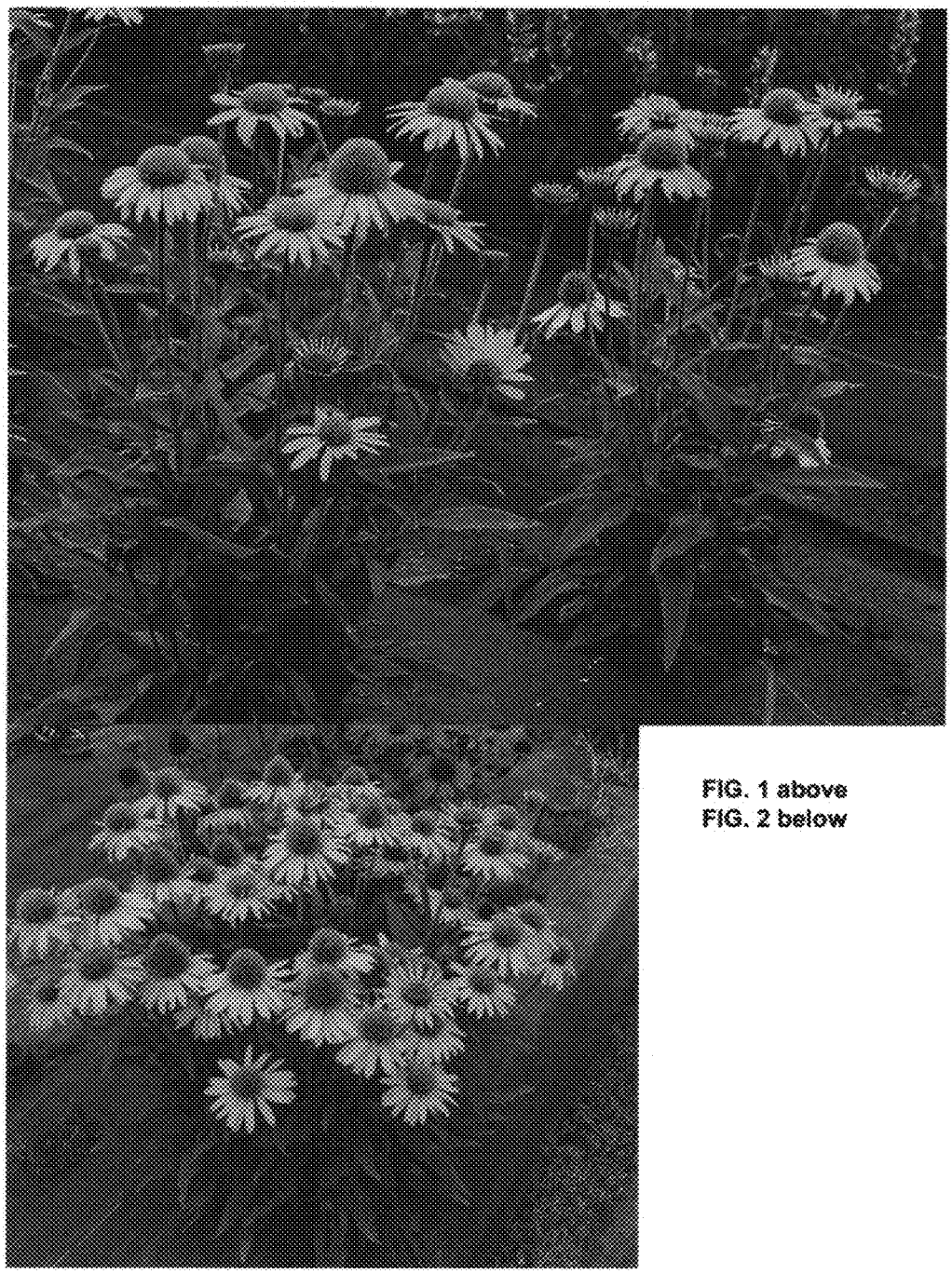
FIG. 1 above
FIG. 2 below